(12) United States Patent
Kanayama

(10) Patent No.: US 7,830,518 B2
(45) Date of Patent: Nov. 9, 2010

(54) AUTOMATIC ANALYSIS APPARATUS AND AUTOMATIC ANALYSIS METHOD

(75) Inventor: Shoichi Kanayama, Tochigi-ken (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 80 days.

(21) Appl. No.: 12/352,337

(22) Filed: Jan. 12, 2009

(65) Prior Publication Data

US 2009/0180120 A1 Jul. 16, 2009

(30) Foreign Application Priority Data

Jan. 11, 2008 (JP) ............................. P2008-004165

(51) Int. Cl.
*G01N 21/00* (2006.01)
(52) U.S. Cl. ...................................... 356/432; 356/440
(58) Field of Classification Search ................ 356/432, 356/439, 440
See application file for complete search history.

(56) References Cited

U.S. PATENT DOCUMENTS 4,014,610 A * 3/1977 Zeineh et al. ............... 356/432
7,701,581 B2 * 4/2010 Forsell et al. ............... 356/440

FOREIGN PATENT DOCUMENTS

JP 2003-149157 5/2003

* cited by examiner

*Primary Examiner*—Roy Punnoose
(74) *Attorney, Agent, or Firm*—Oblon, Spivak, McClelland, Maier & Neustadt, L.L.P.

(57) ABSTRACT

An automatic analysis apparatus and an automatic analysis method analysis that includes an optical convergence point adjusting unit in order to variably adjust an optical convergence point of irradiation light or an optical convergence point of detection light to or from a reaction cuvette in accordance with at least one of analysis conditions of a kind of reaction of a mixed solution contained in the reaction cuvette, a liquid volume of the mixed solution or a measurement wave length. The optical convergence point adjusting unit is provided in front the reaction cuvette, in back of the reaction cuvette, or both in order to variably control the position of an optical convergence point so as to maximize the irradiation light based on the volume of the mixed solution in the reaction cuvette. By variably controlling the convergence point of the optical convergence point adjusting unit based on each of the examination items, both measurements of a turbidimetric assay and a spectrophotometric assay can be performed in a single automatic analysis apparatus with good accuracy and precision.

21 Claims, 9 Drawing Sheets

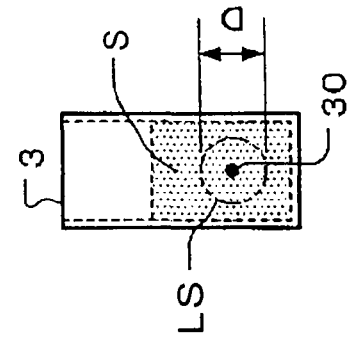
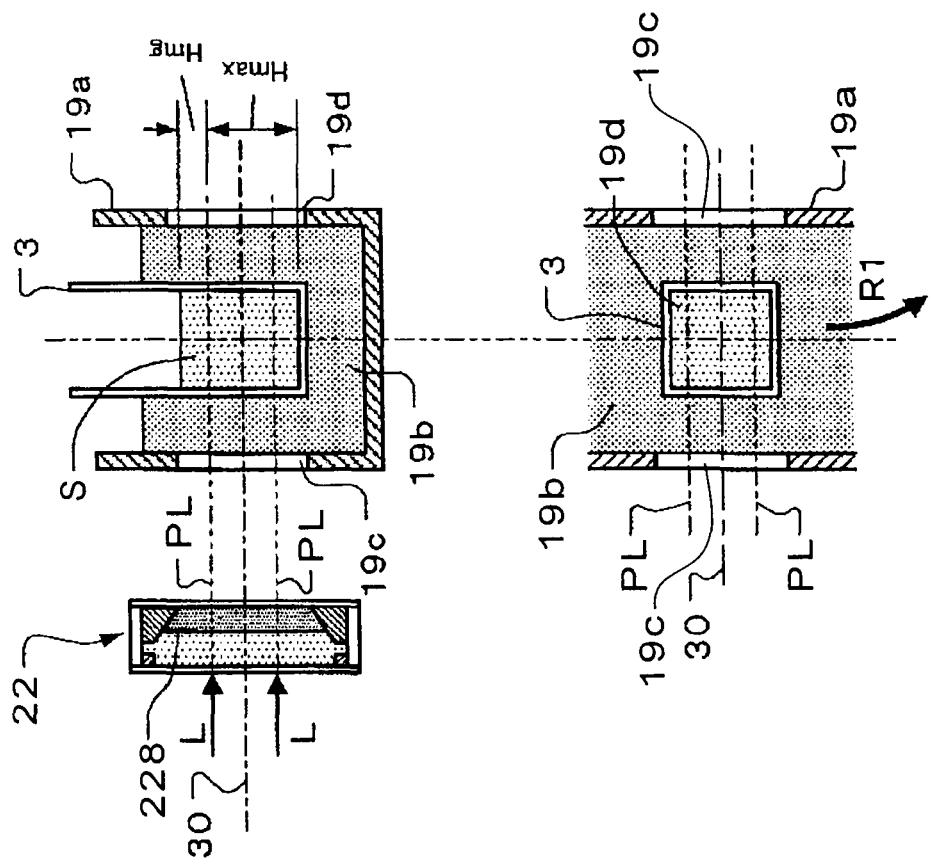

AUTOMATIC ANALYSIS APPARATUS AND AUTOMATIC ANALYSIS METHOD

CROSS REFERENCE TO RELATED APPLICATIONS

This application claims priority from, and the benefit of, Japanese Patent Application No. 2008-4165, filed on Jan. 11, 2008, the contents of which are expressly incorporated herein by reference in their entirety.

BACKGROUND OF THE INVENTION

1. Field of the Invention

Embodiments of the present invention relate to an automatic analysis apparatus and an automatic analysis method for analyzing desired examination items e.g., substances contained in an object sample. More particularly, embodiments of the present invention relate to a highly precise automatic analysis apparatus and an automatic analysis method that can variably change an irradiation area or a detection area for analyzing substances contained in the object sample, such as human humor by adjusting an optical conversion point of the irradiation light into the solution based on one or more designated analyzing conditions.

2. Description of the Related Art

An automatic analysis apparatus mainly measures substances contained in humors such as blood or urine with a biochemical assay or an immune serum assay by adding at least one reagent corresponding to the desired examination item. Generally, an automatic analysis apparatus for performing biochemical tests employs spectrophotometry by analyzing changes in color tone due to light absorption of the mixed solution. Alternatively, an automatic analysis apparatus for performing an immune serum assay employs turbidimetry in order to analyze the concentration of a particular substance in an object sample by measuring a turbidity change with scattered light or transmitted light due to an agglutination that is generated by a reaction between an antigen and an antibody in the mixed solution.

In addition to the turbid metric immunoassay, a latex agglutination turbidimetric immunoassay may also be employed to measure a turbidity change of the object sample due to agglutination that is caused by a reaction between an antigen in an object sample and antibody sensitized latex that is sensitized with latex particles. In either of the turbidimetric immunoassays, a reagent is adjusted so as to be applicable for measurements in a particular immune serum test apparatus.

Recently, an increase o in efficiency and a reduction in cost of the biochemical test and the immune serum test are keenly desired. To meet this desire, it would be desirable to perform a plurality of measurements for a plurality of test items including both the biochemical test and the immune serum test in single analyzing apparatus. Particularly, since automatic analysis equipment for biochemical tests can perform processing for many tests of a plurality of measuring items at high speed, it would be desirable to have an automatic analysis apparatus for the immune serum test.

However, when the automatic analysis apparatus for biochemical tests is applied to measure a turbidity change, measurement accuracy and/or precision decrease due to the effects of multiple scatterings of the dispersion objects in the mixed-solution in a reaction cuvette. Thus, if turbidity changes of immune serum examination items are measured by utilizing transmitted light similar to a spectrophotometric test for bio-chemical examination items, the measurement accuracy and/or precision are reduced since a different absorption degree is calculated from the transmitted light through the mixed solution caused by a difference in the effective length of the light path due to the influence of latex concentrated particles scattered in the mixed solution contained in the reaction cuvette.

To improve measurement accuracy and precision through the transmitted light by reducing such influences due to undesired scattered obstacles and to minimize the volume of reaction solution, the applicant has proposed an automatic analysis apparatus that includes two optical convergence lenses provided in front and back of a reaction cuvette in Japanese patent application publication 2003-149157. In the proposed apparatus, an optical convergence point of the optical convergence lens provided in front of the reaction cuvette is set so as to converge at a predetermined distance behind a center position of the reaction cuvette and the optical convergence point of the optical convergence lens provided in the backside of the reaction cuvette is set to coincide with the optical convergence point of the front optical convergence lens. By setting the convergence point of the optical convergence lens behind the reaction cuvette, the influence of scattered light is reduced by restricting detection of the scattered light due to the latex concentrated scattered particles existing in the mixed solution. Accordingly, the accuracy and precision of turbidimetric measurement by the transmitted light can be improved and also the volume of the mixed solution can be minimized.

In the proposed automatic analysis apparatus, the position of a convergence point of an optical convergence lens is determined so as to obtain the maximum amount of light possible in order to measure a designated minimum volume of a mixed solution for the analysis apparatus in accordance with analysis conditions for a particular examination item. However, once the position of the optical convergence point of the optical convergence lens is set, it is always fixed. Accordingly, other measurements for other examination items under different analysis conditions are also performed at the same position of the optical convergence point that was previously set under a particular analysis condition. Thus, when turbidity change is measured by using the transmitted light, the turbidimetric measurement is executed by fixing the optical convergence point of the optical convergence lens at the same point that is appropriated to obtain an irradiation area for the minimum volume of the mixed solution. Consequently, the measurement accuracy and/or precision are reduced by receiving the influence of obstacles, such as bubbles existing in an isothermal bath for covering the reaction cuvette. This is a serous problem for the turbidimetric measurement.

SUMMARY OF THE INVENTION

Embodiments of the present invention are intended to solve the above-mentioned problems and defects. The automatic analysis apparatus and an automatic analysis method consistent with one embodiment of the present invention includes an optical convergence adjusting unit at either or both an irradiation optical system for irradiating a reaction cuvette and a detection system for detecting light transmitted through a reaction cuvette. The optical convergence adjusting unit is configured to adjust a convergence point (or an image forming point) of irradiation light so as to measure by an optimized irradiation area based on the measurement conditions of a kind of reaction (i.e., the type of test to be performed) and the volume of mixed solution in order to improve the measurement accuracy and precision of both the turbidimetric tests and the spectrophotometric tests. The "optical convergence point" or the "image forming point" is also referred to as "an image information point". The following explanation uses the phrase "optical convergence point" for consistency.

Thus, the present invention provides a new automatic analysis apparatus and an automatic analysis method that can improve both required performance of the spectrophotometric test and the turbidimetric test by adjusting the optical convergence point of the irradiation light based on the respective analysis conditions for each examination item including the volume of reaction solution so as to maximize each irradiation area onto the reaction cuvette in order to avoid the influence of undesired scattering obstacles, such as bubbles. Thus, the automatic analysis apparatus and automatic analysis method consistent with an embodiment of the present invention can avoid the influence of undesirable scattered light and also can minimize the volume of reaction solution for each examination item.

To achieve the above-mentioned objects, one aspect of an embodiment of the automatic analysis apparatus of the present invention includes an optical measurement unit configured to measure substances of examination items in a mixed solution in a reaction cuvette, the mixed solution including an object sample and a reagent by irradiating light and detecting the transmitted light through the reaction cuvette. The optical measurement unit including:

a light source configured to irradiate light through the reaction cuvette along an optical axis of the optical measurement unit;

an optical detection unit configured to detect a prescribed wavelength of light transmitted through the reaction cuvette; and an optical convergence point adjusting unit provided between the light source and the reaction cuvette, or between the reaction cuvette and the detection unit and configured to variably adjust a position of an optical convergence point of the irradiation light on the optical axis based on an analysis condition for the examination items.

The automatic analysis apparatus of another embodiment of the present invention includes an optical measurement unit configured to measure substances of examination items in a mixed solution in a reaction cuvette, the mixed solution including an object sample and a reagent, by irradiating light through the reaction cuvette and detecting the transmitted light through the reaction cuvette, the optical measurement unit including:

a light source configured to irradiate light through the reaction cuvette along an optical axis of the optical measurement unit;

an optical detection unit configured to detect a prescribed wavelength of light transmitted through the reaction cuvette;

a liquid lens provided between the light source and the optical detection unit, the liquid lens includes a plurality of liquid layers having different refractive indexes and a changing unit configured to change an interfacial curvature between the plurality of liquid layers; and a control unit configured to control the changing unit in accordance with each analysis condition for the respective examination items in order to adjust the optical convergence point of the irradiation light through the reaction cuvette.

The automatic analysis method of a further embodiment of the present invention is configured to measure substances of examination items in a reaction solution in a reaction cuvette, the reaction solution including an object sample and a reagent, by irradiating light through the reaction cuvette and by detecting the transmitted light through the reaction cuvette, the optical measurement method including:

variably adjusting an optical convergence point of an optical convergence point adjusting unit provided between the light source and the reaction cuvette, or between the reaction cuvette and the detection optical unit, along an optical axis of the measuring unit based on an analysis condition for the examination items.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 7A illustrates a side view showing an example for supplying parallel light onto a reaction cuvette contained in a thermostatic bath in an embodiment of the automatic analysis apparatus by setting an optical convergence point of the light path at an infinite position through adjusting an inter-surface of a lens in an optical convergence point adjusting unit and a top view of the reaction cuvette.

FIG. 7B illustrates an area of irradiation light on a reaction cuvette viewing along an optical axis shown in FIG. 7A.

DETAILED DESCRIPTION OF THE PREFERRED EMBODIMENTS

Figure 1:
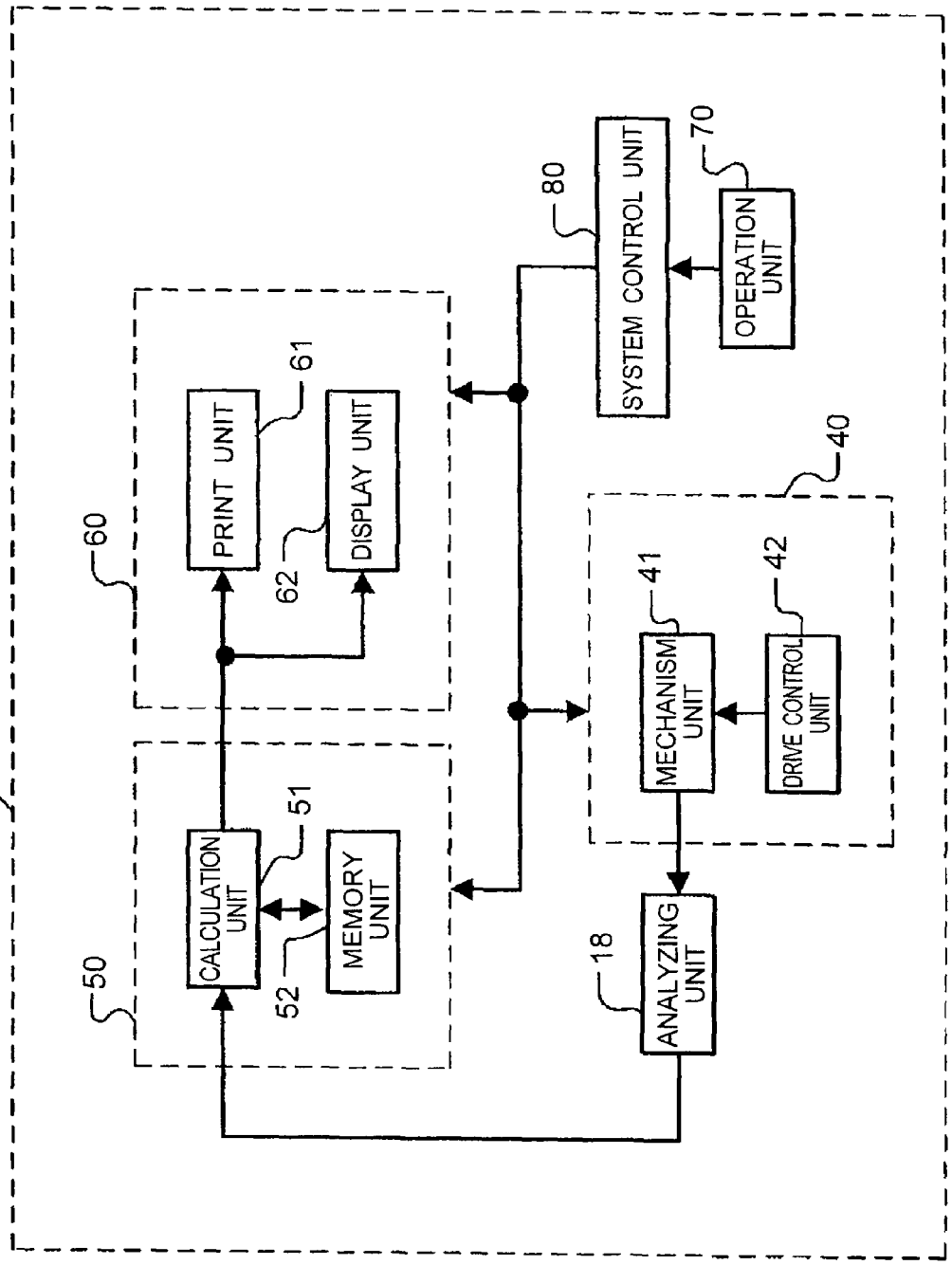
FIG. 1 is a block diagram illustrating an embodiment of an automatic analysis apparatus.

As shown in FIG. 1, an embodiment of an automatic analysis apparatus 100 includes an analyzing unit 18, an analysis control unit 40, a data processing unit 50, an output unit 60, an operation unit 70 and a system control unit 80. The analyzing unit 18, as explained later, includes a plurality of measuring units in order to measure each measuring item for a plurality of reference samples and object samples. The analysis control unit 40 includes a mechanism unit 41 for driving each of measuring units in the analyzing unit 18 and a drive control unit 42 for controlling each drive of the mechanism unit. The data processing unit 50 includes a calculation unit 51 for generating a calibration curve and analysis data based on reference sample data and object sample data supplied from the analyzing unit 18 and a memory unit 52 for storing the calibration curve and the analysis data generated by the calculation unit 51.

The automatic analysis apparatus 100 further includes an output unit 60, an operation unit 70 and a system control unit 80. The output unit 60 includes a print unit 61 and a display unit 62 for inputting the calibration curve and the analysis data generated in the data processing unit 50. The operation unit 70 performs input operations of analysis conditions for a reference sample and a calibration curve for each measuring item and also inputs various kinds of command signals. The system control unit 80 totally controls operations of the analysis control unit 40, the data processing unit 50 and the output unit 60.

Figure 2:
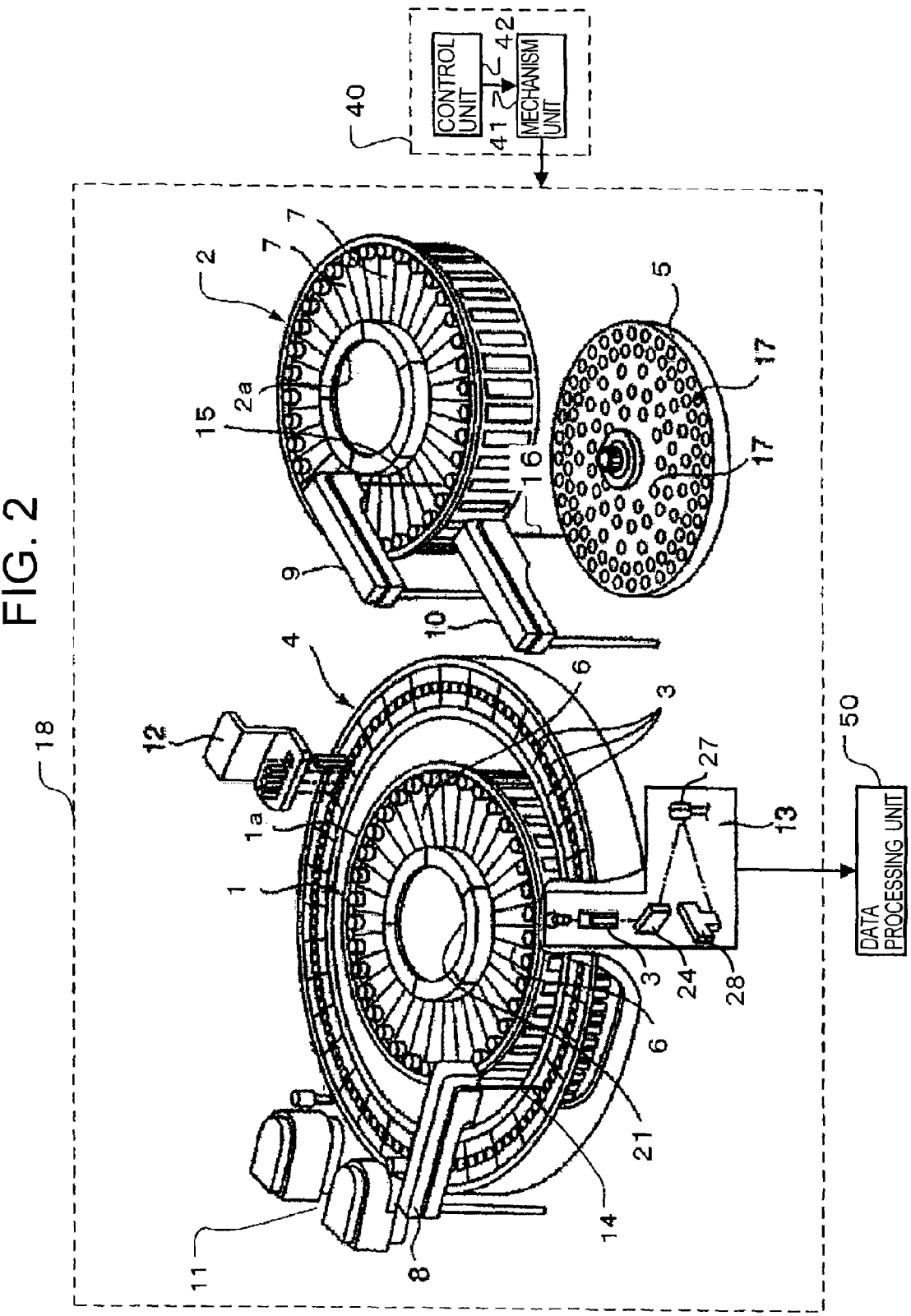
FIG. 2 illustrates an embodiment of the analysis unit in the automatic analysis apparatus shown in FIG. 1.

FIG. 2 shows main components of the analyzing unit 18. The analyzing unit 18 includes a first reagent warehouse 1, a second reagent warehouse 2 and a disk sampler 5. The disk sampler 5 rotatably holds a plurality of sample containers 17 for containing samples, such as a reference sample and an object sample. The first reagent warehouse 1 includes a rack 1a that rotatably holds a plurality of reagent containers 6 containing the first reagent for reacting the substances contained in the sample containers 17 corresponding to the respective items. The second reagent warehouse 2 includes a holding member 2a for rotatably holding reagent containers 7 containing a second reagent that is used as a pair of the first reagent. Typically, when the second reagent is decided to be used, the reagent is a pair of reagents.

The analyzing unit 18 further includes a first dispensing probe 14, a second reagent dispensing probe 15 and a plurality of dispensing probes 14, 15 and 16, each of those probes is rotatably held so as to be moved upward and downward. Thus, the sample dispensing probe 16 is rotatably held by a sample dispensing arm 10 so as to move upward and downward. Similarly, the first dispensing probe 14 and the second reagent dispensing probe 15 are respectively held by first and second reagent dispensing arms 8 and 9 so as to be rotated and moved upward and downward. The sample dispensing probe 16 suctions a sample from a sample container 17 held in the disk sampler 5 and discharges the suctioned sample into a reaction cuvette 3. The first dispensing probe 14 suctions a first reagent from reagent container 6 in the first reagent warehouse I and discharges the suctioned first reagent into reaction cuvette 3. The second reagent dispensing probe 15 suctions a second reagent from a reagent container 7 in the second reagent warehouse 2 and discharges the suctioned second reagent into the reaction cuvette 3 that contains the first reagent.

The analyzing unit 18 further includes a reaction disk 4, a stirring unit 11, a light measuring unit 13 and a washing unit 12. The reaction disk 4 is positioned at an outer surface side of the first reagent warehouse 1 in order to rotatably hold the plurality of reaction cuvettes 3 so as move a particular reaction cuvette at a lighting position. The stirring unit 11 stirs a mixed solution of a sample and a first reagent or a mixed solution of a sample and both a first reagent and a second reagent that are dispensed into a reaction cuvette 3. The light measuring unit 13 measures the reaction cuvette 3 containing each of the mixed solutions. The washing unit 12 includes a washing nozzle for suctioning each mixed solution that remains in a reaction cuvette 3 after a measurement and for washing an inside of the reaction cuvette 3. The drying nozzle is held so as to move upward and downward. Thus, after a measurement, the reaction cuvette 3, the sample dispensing probe 16, the first and second reagent dispensing probes 14 and 15 and the stirring unit 11 are used for a next measurement after washing.

The light measuring unit 13 irradiates light to a rotatably moving reaction cuvette 3 at a light measuring position P in order to generate reference sample data that is converted to light transmitted in the mixed solution including a light reference sample into a light absorption degree. The absorption degree is outputted to the data processing unit 50. The light measuring unit 13 further generates object sample data by converting transmitted light in the mixed solution including an object sample into a light absorption degree and outputs object sample data to the data processing unit 50. The washing unit 12 includes a washing nozzle for suctioning each mixed solution that remains in a reaction cuvette 3 after a measurement and for washing the inside of the reaction cuvette 3. The drying nozzle is held so as to move upward and downward. Thus, after a measurement, the reaction cuvette 3, the sample dispensing probe 16, the first and second reagent dispensing probes 14 and 15 and the stirring unit 11 are used for a next measurement after washing.

The analysis control unit 40 includes a mechanism unit 41 having a drive mechanism for driving each of the measuring portions of the analyzing unit 18 and a control unit 42 for controlling each portion of the mechanism unit 41 by driving each of the mechanisms. The mechanism unit 41 includes a rotating mechanism for respectively rotating a first rack 1a of the first reagent warehouse 1, a second rack 2a of the second reagent warehouse 2 and the disk sampler 5, a mechanism for rotating the reaction disk 4 and for rotating and driving upward and down ward a sample dispensing arm 10, a first reagent dispensing arm 8, a second reagent dispensing arm 9 and a stirring unit 11, and also for moving upward and down ward the washing unit 12.

The mechanism unit 41 further includes a sample dispensing pump driving mechanism for suctioning and discharging a sample solution through the sample dispensing probe 16, a first and second reagent pump driving mechanism for suctioning and discharging the first and second reagent from the first and second reagent dispensing probes 14 and 15, a stirring drive mechanism for stirring a member in the stirring unit, a drive mechanism for driving each portion of the light measuring unit 13, a washing pump drive mechanism for suctioning a mixed solution and for discharging and suctioning a washing liquid from a washing nozzle of the washing unit 12 and a drying pump driving mechanism washing unit 12 for suctioning from a drying nozzle.

The data processing unit 50 includes a calculation unit 51 and a memory unit 52. The calculation unit 51 generates a calibration curve based on reference sample data of each measuring item supplied from each light measuring unit 13 in the analyzing unit 18. The generated curve is stored in the memory unit 52 and also outputted to the output unit 60. The memory unit 52 is comprised of, for instance, a hard disk, and stores each calibration curve outputted from the calculation unit 51 for each measuring item. The calculation unit 51 further generates density or activity analyzing data by using a calibration curve corresponding to a measuring item of an object sample data read out from the memory unit 52. The analyzing data generated from the calculation unit 51 area is stored in a hard disk of the memory unit 52 for each of the object samples and also outputted to the output unit 60.

Such a calibration curve or analysis data supplied from the data processing unit 50 is printed by a print unit 61 in the output unit 60. The print unit 61 provides a printer in order to print the calibration curve or analysis data on printing paper under a prescribed format. The output unit 60 further includes a display unit 62. The display unit 62 includes a monitor, such as a cathode ray tube (CRT) or a liquid crystal panel (LCP) in order to display a calibration curve and analysis data outputted from the data processing unit 50. Further, the monitor displays an analysis conditions setting screen for setting analysis conditions of each measuring item, such as sample volume, reagent volume and wavelength of light. The monitor also displays an object setting screen for settings such as the object ID and the name of the object, and a measuring item selection screen for selecting measuring items for each of the object samples.

The operation unit 70 includes input devices, such as a key board, a mouse, buttons, and a touch key panel for inputting data such as analysis conditions for each measured item, object data such as object ID and name of the object, and measuring items for each of the object samples.

The system control unit 80 includes a central processing unit (CPU) and a memory circuit. The memory circuit in the system control unit 80 stores data, such as command signals inputted through the operation unit 70, various analysis conditions for each measuring item, object data, and measuring items for each of the object samples. By this stored data, the CPU in the system control unit 80 totally controls the whole operation of the automatic analysis apparatus.

Figure 3:
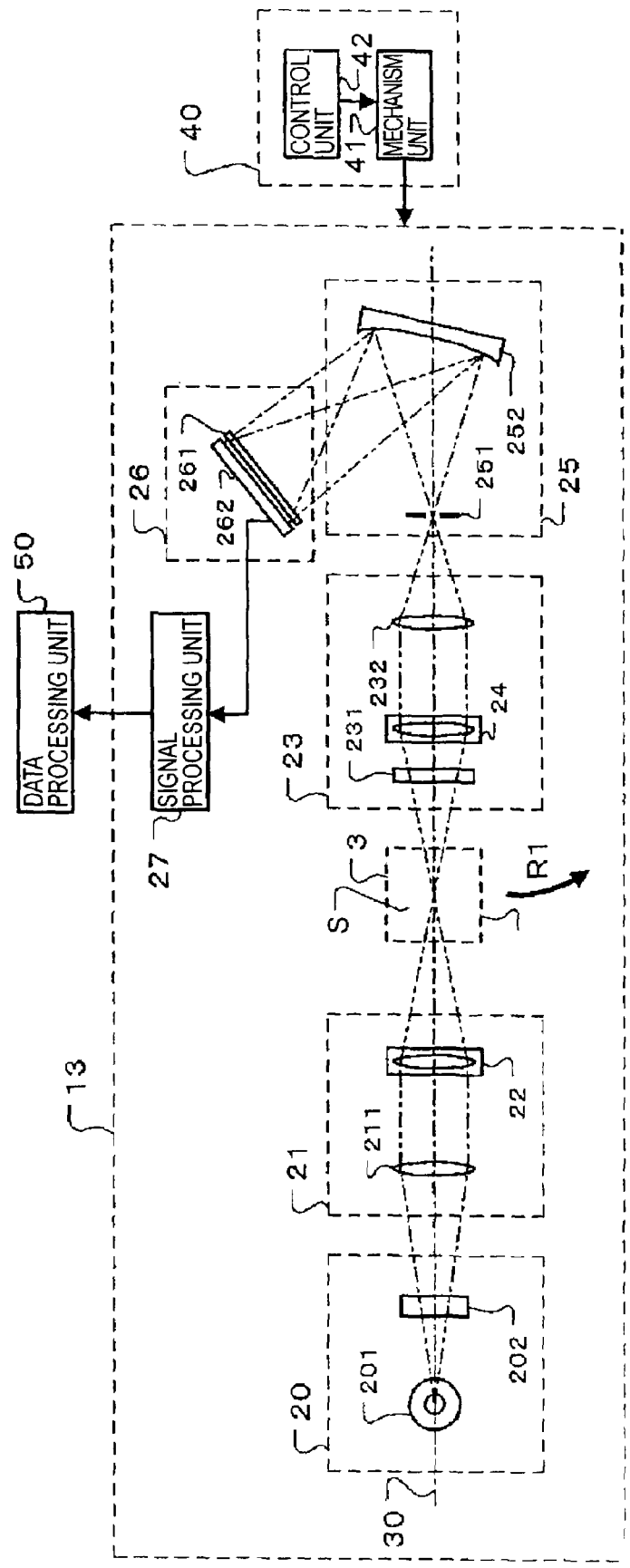
FIG. 3 illustrates an embodiment of the measuring unit in the automatic analysis apparatus shown in FIG. 1.

FIG. 3 shows a construction of the light measuring unit 13 in the analyzing unit 18. The light measuring unit 13 includes a light source unit 20 for emitting light, an irradiation optical system unit 21 for irradiating the emitted light from the light source unit 20 onto a reaction cuvette 3 positioned at a measuring position P, a detecting optical system unit 23, a spectroscopic analysis unit 25, a light detection unit 26 and a signal processing unit 27. The light source unit 20 includes a white light source unit and a monochromatic light source unit. The light source unit 20 includes a white light source 21 for irradiating white light. The white light source unit is comprised of a white light source 201 of, for instance, a halogen lamp that irradiates white light including a wide range of wavelengths from near ultraviolet to near infrared and an optical filter 202 for cutting off unnecessary light from the white light source, such as heat rays. The white light source is provided so that an emission center of the white light is located on a light axis 30.

The irradiation optical system unit 21 is comprised of a first lens 211, such as a collimating lens which collimates the emitted light from the light source unit 20, so as to, for example, be parallel to the light axis 30 and a front optical convergence adjusting unit 22 provided between the first lens 211 and the cuvette 3 so as to be apart from the cuvette 3. As is explained later, the front optical convergence adjusting unit 22 can variably adjust the optical converging position of the irradiation light onto the cuvette 3.

Figure 4A:
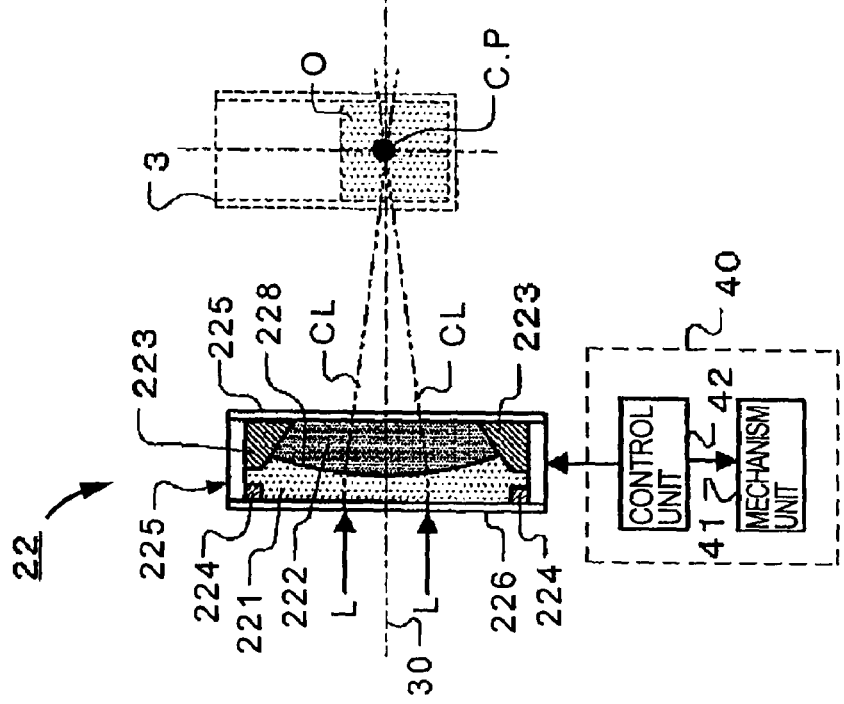
FIG. 4A illustrates a construction of an optical convergence point adjusting unit of an embodiment of the automatic analysis apparatus so that parallel irradiation light along an optical axis is supplied onto a reaction cuvette.
Figure 4B:
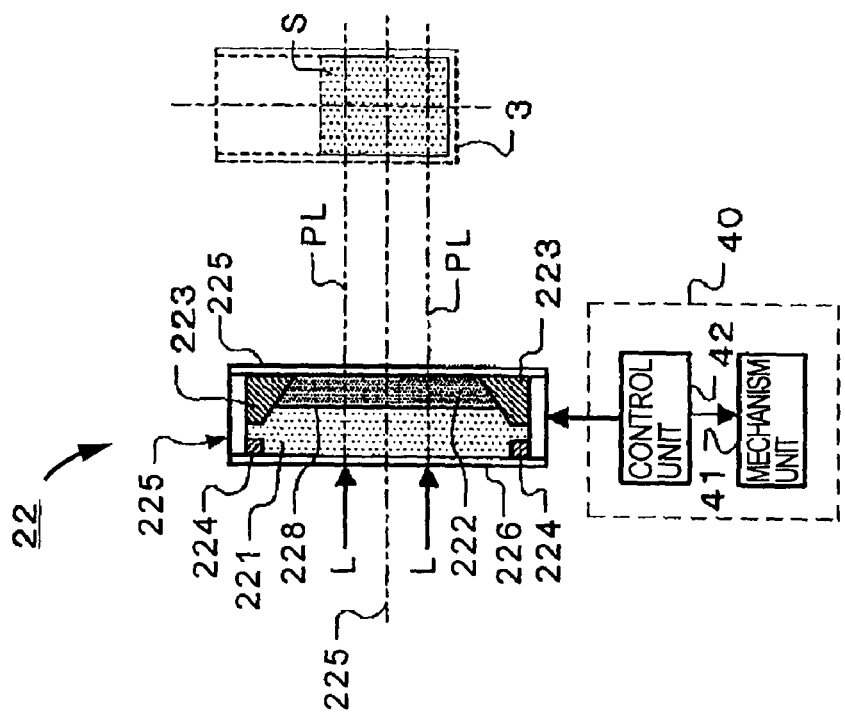
FIG. 4B illustrates an optical convergence point at about the center in the reaction cuvette shown in FIG. 4A by adjusting an interfacial curvature of the lens in the optical convergence point adjusting unit in order to obtain a sufficient light area for measuring a minimum volume of liquid.

FIGS. 4A and 4B illustrate an embodiment of an optical convergence point adjusting unit 22. The optical convergence point adjusting unit 22 is comprised of a liquid lens of two layers including a liquid layer 221 and an oil layer sealed in a case 225. Each of the two layers has a different refractive index and includes at least one inter-surface 228 between them. The optical convergence point adjusting unit 22 is further comprised of a changing unit including a pair of electrodes 223 and 224 configured to change the curvature of inter-surface 228. The pair of electrodes 223 and 224 is provided so as to face each other through the liquid lens of two layers. Each pair of electrodes 223 and 224 includes a circular or square aperture so as to pass the irradiation light through the liquid lens. It is also possible to construct the liquid lens with first and second oil layers each having a different refractive index.

The pair of electrodes 223 and 224 changes the curvature of the inter-surface 228 in the liquid lens of two layers by a control voltage supplied from the analysis control unit 40. The curvature of the inter-surface 228 between the liquid layer 221 and the oil layer 222 can be changed by adjusting the control voltage so as to variably adjust the optical convergence point of the irradiation light to the reaction cuvette 3 on the optical axis of the measurement unit.

The case 225 of the optical convergence point adjusting unit 22 includes a first transmission window 226 facing the first collimator lens 211 in the optical irradiation unit 21 and a second transmission window 227 facing the reaction cuvette 3. The light L irradiated to the first transmission window 226 through the first collimator lens 211 is transmitted through the liquid layer 221 and the oil layer 222 in the liquid lens and the second transmission window 227 in order to irradiate a reaction cuvette 3. Reaction cuvette 3 arrived at a measuring position by being rotated in the analysis unit along an RI direction as shown in FIG. 3.

Based on each analysis condition for the respective examination items of the mixed solution dispensed in the reaction cuvette 3, the position of the optical convergence point C.P. of the irradiation light onto the reaction cuvette 3 is variably controlled through the control unit 42 in the analysis control unit 40. In this embodiment, the curvature of the inter-surface 228 between the liquid layer 221 and the oil layer 222 is varied by controlling a voltage supplied to the pair of electrodes 223 and 224 depending on a parameter of distance data from the center position of the reaction cuvette 3 on the optical axis 30 in the measuring unit to the optical convergence point C.P. It is also possible to adjust the curvature of the inter-surface 228 in the liquid lens by using a numeral aperture (NA) as the parameter.

FIG. 4A illustrates adjusting the curvature of inter-surface 228 so that an optical convergence point is set at an infinite distance from the center position of a reaction cuvette 3 in order to form a light P.L. of an irradiation light L onto a reaction cuvette 3 that is substantially parallel in the reaction cuvette 3 along an optical axis 30. FIG. 4B illustrates a state that the curvature of inter-surface 228 in a liquid lens 22 is varied so as that the irradiation light L to the reaction cuvette 3 converges at a center position O in the reaction cuvette 3 by setting zero (0) as the distance from the center position in the reaction cuvette 3 to the optical convergence point C.P. By setting the optical convergence point O of the irradiation light L at the center position in the reaction cuvette 3, it becomes possible to measure a minimum liquid volume of a mixed solution. In a case that a liquid volume of the mixed solution in the reaction cuvette 3 is larger than the minimum liquid volume, the optical convergence point can be changed to another position on the optical axis by setting a finite distance other than zero (0) from the center position in the reaction cuvette 3 to the optical convergence point of the irradiation light L.

It is also possible to construct the optical convergence point adjusting unit 22 including a plurality of lenses and a moving mechanism for moving the plurality of lenses along the optical axis 30 so as to change the position of the optical convergence point of the irradiation light onto the reaction cuvette.

The optical detection unit 23 is comprised of a shutter 231 configured to shut the irradiation light from the optical irradiation unit 21, an optical convergence point adjusting unit 24 configured to variably change the position of the optical convergence point in order to converge the transmitted light through the mixed solution contained in the reaction cuvette 3 and the second lens 232 for illuminating the light converged by the optical convergence point adjusting unit 24 to a spectroscopic analysis unit 25. In the optical detection unit 23, an optical convergence point adjusting unit 24 is provided between the shutter 231 and the second lens 232.

The shutter 231 in the optical detection unit 23 is used for obtaining output signals from the detection unit 26 by operating in accordance with open and close movements by the mechanism unit 41 in the analysis control unit 40. To obtain an output signal of the transmission ratio of zero %, the shutter 231 is closed in order to cut off the irradiation light from the optical irradiation unit 21. To measure a sample, the shutter 231 is opened in order to transit the irradiation light transmitted through the mixed solution contained in the reaction cuvette 3.

While the optical convergence adjusting lens unit 24 in the optical detection system is comprised of the same structure of the optical convergence adjusting lens unit 22 in the optical irradiation unit 21 as shown in FIGS. 4A and 4B, each of the transmission windows are provided so as to face the opposite sides of the optical convergence adjusting lens unit 22. Thus, a transmission window of the optical convergence adjusting lens unit 24 corresponding to the second transmission window 227 provided at a backside of the oil layer 222 of the optical convergence adjusting lens unit 22 in the optical irradiation system is provided so as to face a reaction cuvette 3 in the optical detection system. The control unit 42 in the analysis control unit 40 decides an optical convergence point of the optical convergence adjusting lens unit 24 in the optical detection system by linking the optical convergence adjusting lens unit 22 in the optical irradiation system 21.

When the optical convergence point of the optical convergence adjusting lens unit 22 in the optical irradiation system is positioned at an infinite distance on the optical axis from the center position in the reaction cuvette 3, the optical convergence point of the optical convergence adjusting lens unit 24 in the optical detection system is adjusted so as to be positioned at the optical convergence point of the optical convergence adjusting lens unit 22. When the irradiation light from the optical convergence adjusting lens unit 22 in the optical irradiation system is parallel light, the optical convergence adjusting lens unit 24 in the optical detection system adjusts the light path so as to coincide with the parallel light. In this case, the second lens 232 in the optical detection unit 23 converges the parallel light from the optical convergence adjusting lens unit 24 in the optical detection system onto the spectroscopic analysis unit 25.

The spectroscopic analysis unit 25 (FIG. 3) is comprised of a slit 251 configured to narrow down the light passed through the second lens 232 in the optical detection unit 23 to a prescribed area, and a diffraction grating 252 for grating the light through the slit 251. The slit 251 is provided at about the position of an optical convergence point of the second lens 232 and narrows down so that the light from the second lens 232 enters in an effective range of the diffraction grating 252. The diffraction grating 252 separates the light irradiated from the slit 251 in a prescribed direction for each wavelength.

The detection unit 26 is comprised of a filter array 261 for avoiding stray light and a photo-diode array 262 including a plurality of light receiving elements for detecting the transmitted light through the filter array 261 in each of a plurality of wavelengths under preliminarily determined wavelengths. The photo-diode array 262 detects the light of a plurality of wavelengths separated in the respective wavelength by the diffraction grating 252 in the spectroscopic analysis unit 25 and converts the plurality of separated lights into electrical signals. The converted electrical signals are outputted to a signal processing unit 27.

The signal processing unit 27 performs analog/digital conversions of the detection signals outputted from the photo-diode array 262 in the detection unit 26 and generates the reference sample data and object sample data indicating absorption degrees. These data are outputted to a data processing unit 50.

Figure 5:
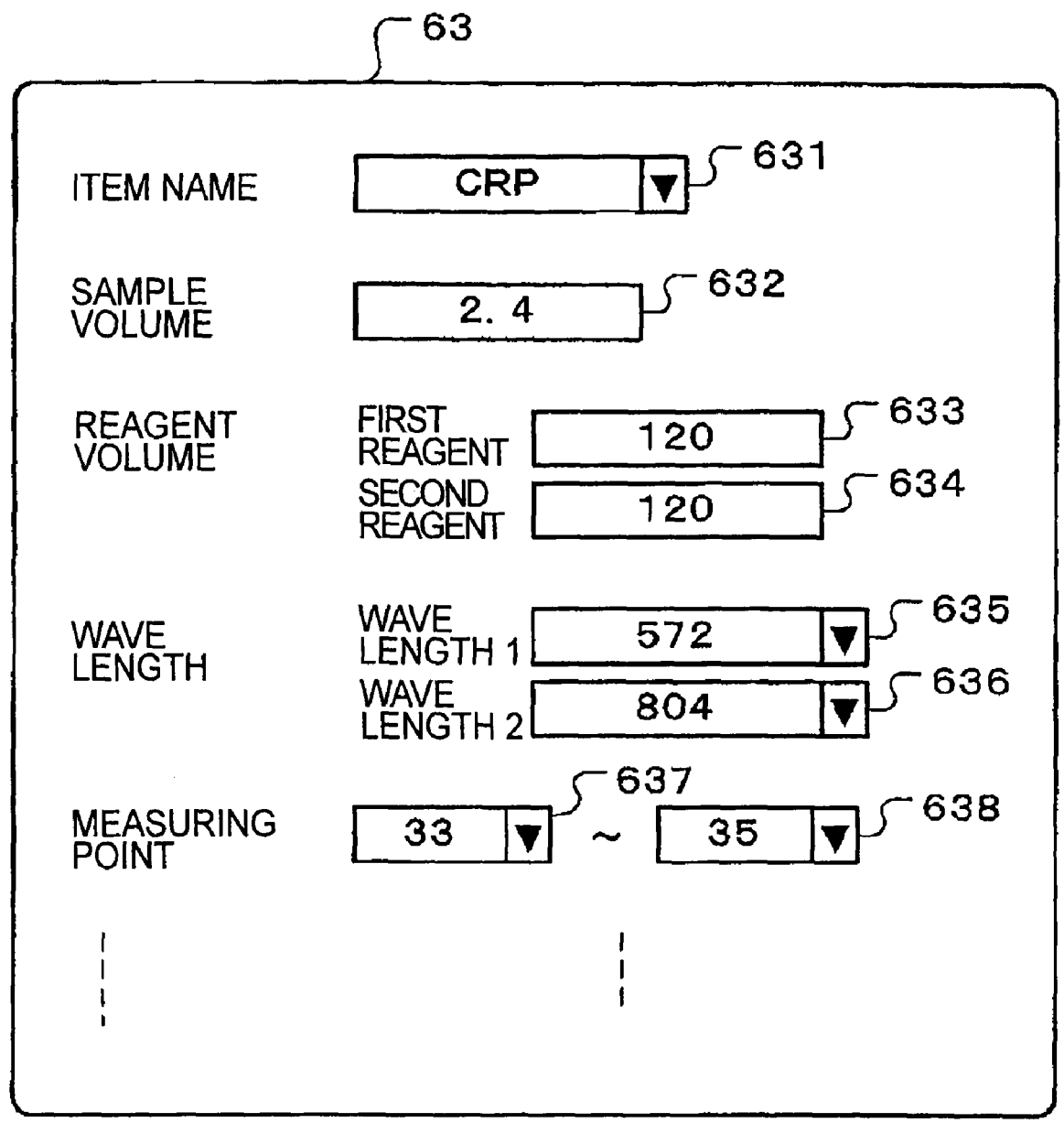
FIG. 5 illustrates an example of a setting screen of analysis conditions for a turbidity measurement in an embodiment of the automatic analysis apparatus.

FIG. 5 shows an example of analysis conditions setting screen 63 displayed on the display unit 62. The analyzing conditions setting screen 63 displays a plurality of dialogue boxes 641 to 649 for displaying a plurality of setting data based on a plurality of input operations of instructions. As an example of the turbidimetric immunoassay item, it is supposed that a C-Reactive Protein is inputted and "CRP" is displayed in the "item name" dialogue box 631. To measure the CRP, for instance, an object sample of volume 3 µl is inputted. Accordingly, a numeral "3" is displayed in the "sample volume" dialogue box 632.

The "reagent volume" column includes a "first reagent" dialogue and a "second reagent" dialogue. When an examination item designated in the "item name" dialogue box 631 is measured by a single reagent, the volume is set only in the "first reagent" dialogue. When an examination item designated in the "item name" dialogue box 631 is measured by two reagents, each volume of reagent dispensed in a reaction cuvette 3 is set in both the "first reagent" dialogue and the "second reagent" dialogue. In the example shown in FIG. 5, since the C-Reactive Protein is measured by two reagents, both the "first reagent" dialogue box 633 and the "second reagent" dialogue box 634 are each respectively designated a volume of 120 µl by inputting the number 120.

The "wavelength" column includes a "wavelength 1" column and "wavelength 2" column for setting each detection wavelength corresponding to the kind of reaction of the examination item, i.e. a chromatic change or a turbidity change designated in the "item name" column. One or two different wavelengths are set by selecting among the prescribed plurality of wavelengths. For example, when a wavelength of 572 nm is inputted in the "wavelength 1" column by a selection operation in accordance with the kind of reaction of the examination item "CRP" designated in the "item name" column, a numeral "572" is displayed in the dialogue box 635. Similarly, if a wavelength of 804 nm is inputted in the "wavelength 2" column in accordance with the kind of reaction for the examination item "CRP", a numeral "804" is displayed in the dialogue box 636.

At a "light measuring point" item, the measuring points selected for the mixed solution containing C-Reactive Protein are inputted. For instance, when the thirty-third to thirty-fifth light measuring points are inputted, numerals "33" and "35" are respectively displayed in the dialogue boxes 637 and 638. Thus, a total of three measurements are performed at each of the thirty-third to thirty-fifth light measuring points when the reaction cuvette 3 containing the measuring mixed solution passes the light measuring position P. Accordingly, the light measuring unit 13 generates three object data samples for the "CRP" and analysis data is generated based on the object sample data.

FIGS. 6-9 illustrate examples of variable position control of the optical converging point of the optical convergence adjusting lens unit 22 in the optical irradiation unit 21 and the optical convergence adjusting lens unit 24 in the optical detection unit 23 based on the analysis condition designated for the various examining substances. In the following, the explanation is only made as to the optical converging point of the optical convergence adjusting lens unit 22 in the optical irradiation system. In each case, the optical converging point of the optical convergence adjusting lens unit 24 in the optical detection system is supposed so as to be adjusted at the same position of the optical convergence adjusting lens unit 22 in the optical irradiation system.

Figure 6:
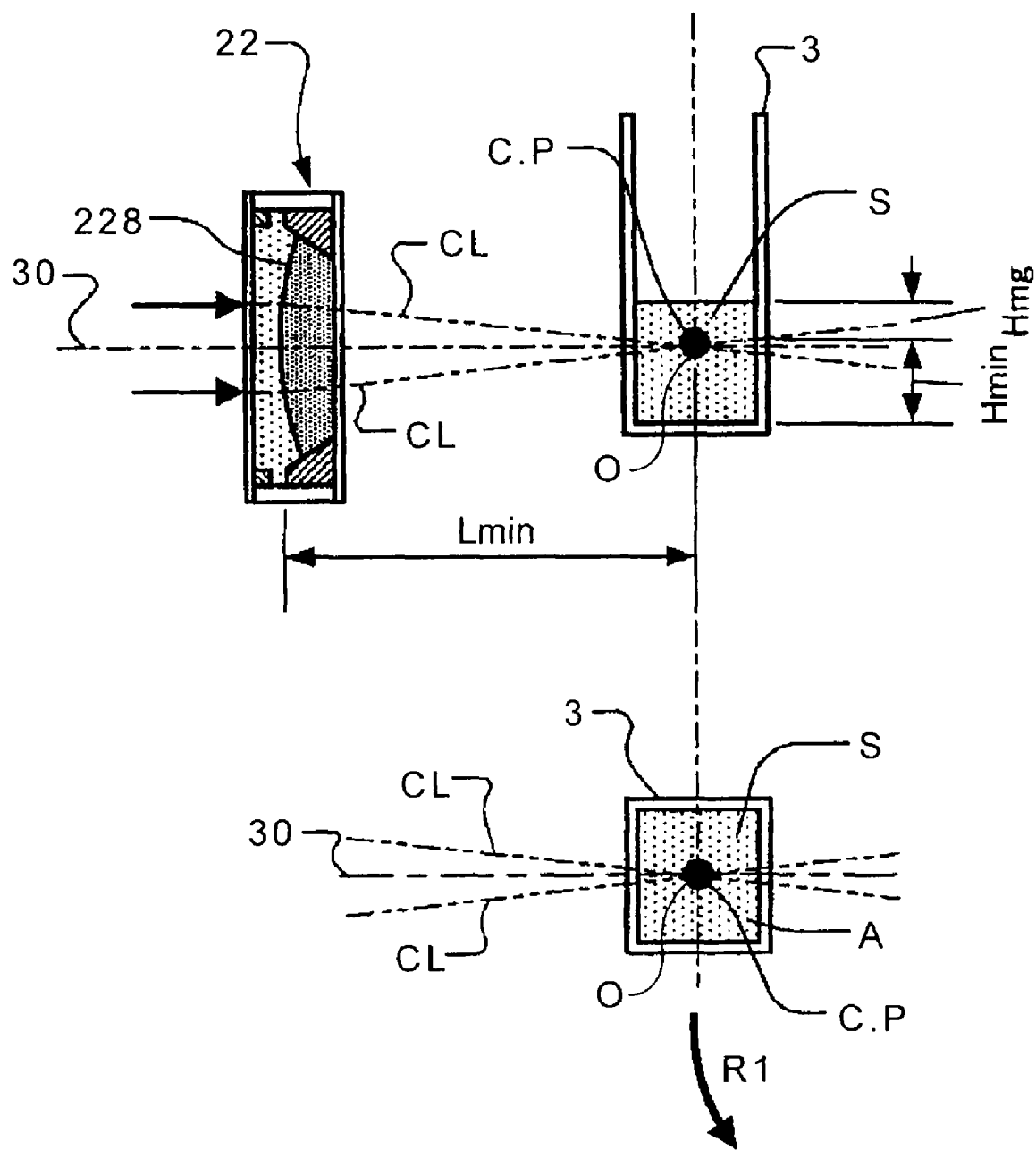
FIG. 6 illustrates a side view showing an example for setting an optical convergence point of a light path at a about the center in a reaction cuvette in an embodiment of the automatic analysis apparatus by adjusting an inter-surface of a lens in an optical convergence point adjusting unit and a top view of the reaction cuvette.
Figure 8:
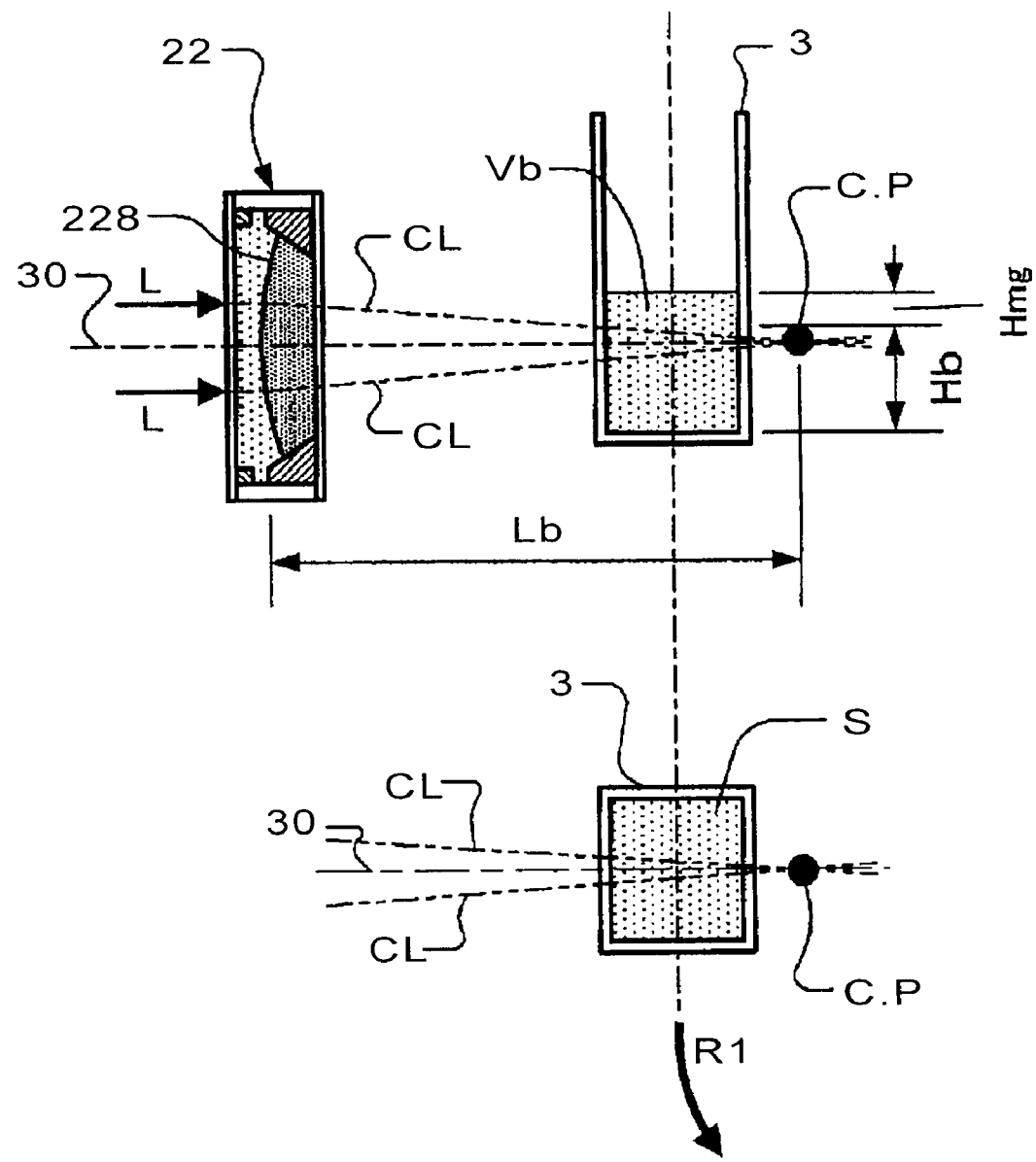
FIG. 8 illustrates an example for setting an optical convergence point of the light path at a position behind the reaction cuvette by adjusting an inter-surface in a lens of an optical convergence point adjusting unit in an embodiment of the automatic analysis apparatus.
Figure 9:
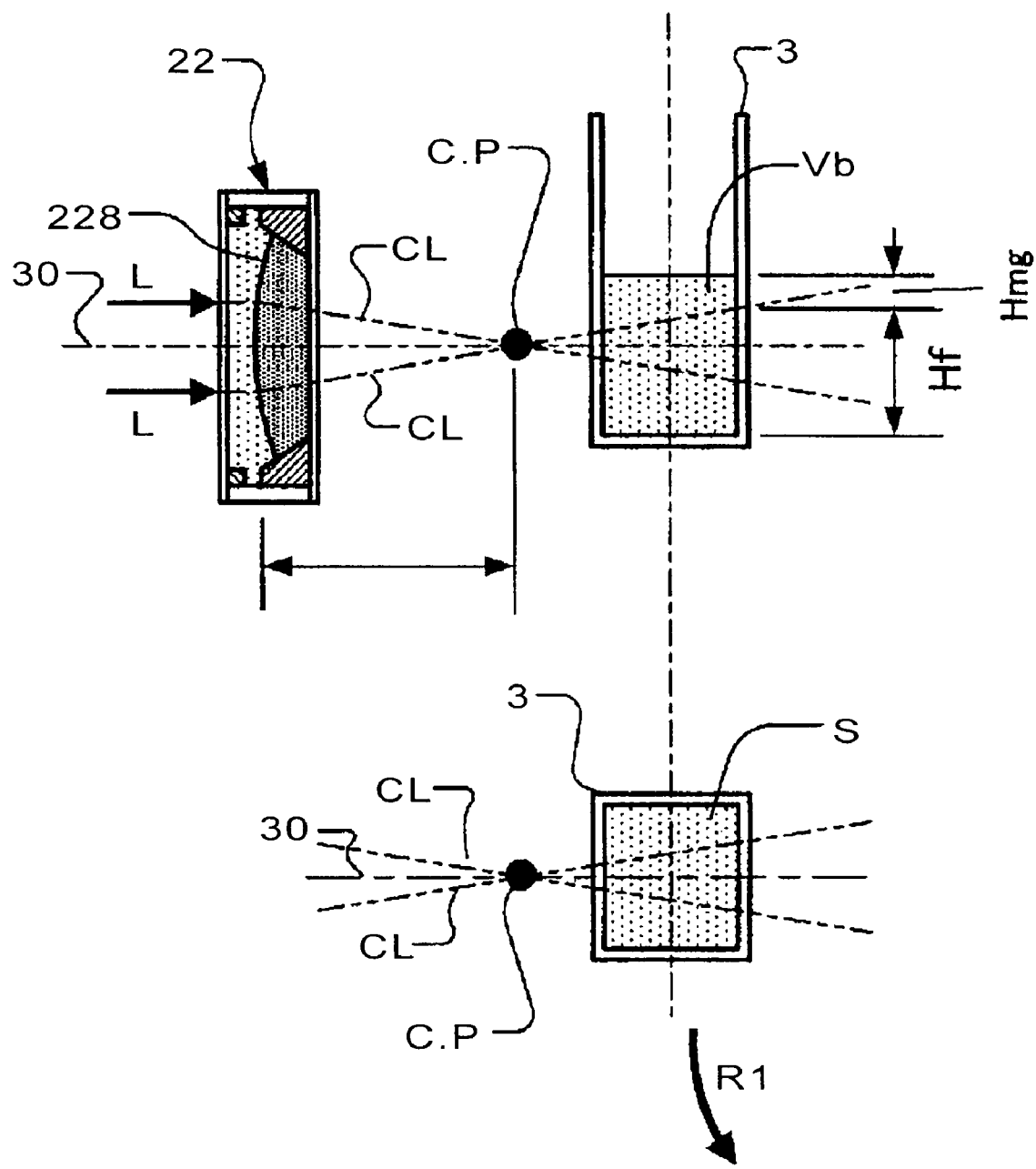
FIG. 9 illustrates an example for setting an optical convergence point of a light path at a position in front of a reaction cuvette by adjusting an inter-surface in a lens of an optical convergence point adjusting unit in an embodiment of the automatic analysis apparatus.

FIG. 6 illustrates a first case where an optical converging point of the optical convergence adjusting lens unit 22 is designated so as to converge at the center position of the reaction cuvette 3. FIG. 7a illustrates a second case where an optical converging point of the optical convergence adjusting lens unit 22 is designated so as to converge at an infinite distance from the center position of the reaction cuvette 3. FIG. 7B illustrates an irradiation area of a parallel light P.L. on the reaction cuvette 3 viewed from the light axis direction shown in FIG. 7A. FIG. 8 illustrates a third case where an optical converging point of the optical convergence adjusting lens unit 22 is designated so as to converge at a definite position behind the reaction cuvette 3 on the light axis. FIG. 9 illustrates a fourth case where an optical converging point of the optical convergence adjusting lens unit 22 is designated so as to converge at a definite position in front of the reaction cuvette 3 on the light axis.

The optical converging point C.P. of the optical convergence adjusting lens unit 22 is variably adjusted based on at least one of the data that includes analysis conditions inputted through the analysis conditions setting screen 63, such as, a sample volume, a reagent volume and a detection wavelength, and preliminary designated analysis conditions designated for the respective examining substances, such as the kind of reaction and the properties of the reagent liquid. The following embodiment is explained by supposing that an optical convergence adjusting lens unit 22 is variably adjusted for performing the measurement of an examining substance "CRP" by the turbidimetric measurement.

The preliminary designated analysis condition data for the respective examining substances inputted through an analysis conditions setting screen 63, such as a kind of reaction and reagent liquid characteristics, are stored in a memory circuit in the system control unit 80. Thus, when an examining substance "CRP" is designated by the analysis conditions setting screen 63, the turbid metric measurement data is stored in the memory circuit in the system control unit 80 as the "kind of reaction" for measuring the item "CRP". The control unit 42 in the analysis control unit 40 controls the optical convergence adjusting lens unit 22 based on the analysis conditions for the item "CRP" supplied from the system control unit 80. Under the control of the control unit 42, the optical convergence adjusting lens unit 22 converges the irradiation light onto a reaction cuvette 3 in accordance with the total volume of a reactive solution including both a sample volume and reagent volumes that are respectively designated in the "sample volume" column and the "reagent volume" column designated in the analysis conditions setting screen 63.

As illustrated in FIG. 6, when the optical convergence adjusting lens unit 22 adjusts the irradiation light so as to converge at center the position O in a reaction cuvette 3, the parallel light L supplied from collimator lens 211 in the optical irradiation unit 21 converges at the center position O. The center position O is a distance Lmin from the crossing point between a center of the inter-surface 228 and the light axis 30. The converged light transits the reaction cuvette 3.

The light path area in the reaction cuvette 3 has a minimum height Hmin at a highest flat portion from a bottom surface in the reaction cuvette 3. As shown in the top view of the reaction cuvette 3, the bottom surface of the reaction cuvette 3 has a bottom area A of, for example a square.

Since the upper surface of the mixed solution contained in the portion of reaction cuvette 3 has buildup at a reaction cuvette contacting surface due to surface tension, the measurably flat portion of the solution surface is lower than the calculated liquid height of the mixed solution. Accordingly, a tolerance height Hmg is required in order to avoid inclusions of obstacles, such as air, into the light path due to the surface tension at an upper portion of the mixed solution. Thus, a necessary minimum liquid height for a measurement needs to add the tolerance height Hmg to the minimum height Hmin, i.e., a total height (Hmin+Hmg). Accordingly, the minimum liquid amount Vmin for measuring the mixed solution in the measurement unit 13 becomes a product ((Hmin+Hmg)×A), wherein A is an area of the reaction cuvette. Thus, when the minimum liquid volume Vmin is designated as the volume of the reaction solution through the analysis conditions setting screen 63, the optical converging point of the optical convergence adjusting lens unit 22 is controlled so as to be positioned at the center position O in the reaction cuvette 3 by the analysis control unit.

When the turbidimetric measurement is selected as the kind of reaction for the examining substance designated by the analysis conditions setting screen 63, if the total liquid volume of the sample volume and the reagent volume that are designated by the analysis conditions setting screen 63 becomes the minimum liquid volume Vmin, it can from the turbidimetric measurement by optically converging at the center of the reaction cuvette 3.

FIGS. 7A and 7B illustrate a case where the optical convergence adjusting lens unit 22 can adjust an optical converging point at an infinite distance from the center position of the reaction cuvette 3 reaction in accordance with a designated liquid volume of the reactive solution by the analysis conditions setting screen 63. When the optical convergence adjusting lens unit 22 adjusts an optical convergence point at an infinite distance from the reaction cuvette 3, the irradiation light L from the collimator lens 211 in the optical irradiation unit 21 goes straight into the reaction cuvette 3 after transmitting through the optical convergence adjusting lens unit 22 maintaining a parallel light path. At this time, a light path area in the reaction cuvette 3 is formed at the highest position Hmax from the bottom surface in the reaction cuvette 3. This case is also required a tolerance height Hmg in order to avoid the influence of surface tension. Accordingly, it is required to have a total liquid height (Hmax+Hmg) by adding the highest height Hmax of the light path and the tolerance height Hmg. If the reaction cuvette 3 has an area A, a maximum liquid volume Vmax is obtained by the product ((Hmax+Hmg)×A). Accordingly, it becomes possible to measure by parallel light when the liquid volume in the reaction cuvette 3 exceeds the maximum liquid volume Vmax. Thus, if the volume of the reactive solution designated in the analysis conditions setting screen 63 exceeds the maximum liquid volume Vmax, parallel light P.L. is irradiated onto the reaction cuvette 3 by controlling an optical converging point of the optical convergence adjusting lens unit 22 so as to position at an infinite distance from the reaction cuvette 3.

According to the automatic analysis apparatus according to the present invention, it becomes possible to maximize the irradiation projecting area by controlling both optical converging points of the optical convergence adjusting lens unit 22 in the optical irradiation system and the optical convergence adjusting lens unit 24 in the optical detection system in accordance with the liquid volume of the reactive solution included in the analysis conditions. If the liquid volume of the reactive solution designated in the analysis conditions setting screen 63 exceeds the maximum liquid volume Vmax, parallel light can be irradiated onto the reaction cuvette 3 and the measurement can be executed by converging the parallel light transmitted through the mixed solution. Consequently, it becomes possible to restrain the influences of scattered light that creates error factors in the measurement of the turbidity change by using the transmission light. Further, since the light energy transmitted in the isothermal bath can be reduced and also the influence of bubbles existing in the isothermal bath can be reduced, the accuracy and precision of the measurement can be improved.

In FIG. 7, the reaction cuvette 3 is kept at a constant temperature by circulating isothermal water 19b contained in the isothermal bath 19a. As illustrated in FIG. 7B, when the light path onto the reaction cuvette 3 is viewed in a direction of the light axis 30, the light from the optical convergence adjusting lens unit 22 transmits through isothermal water 19b and the first transmission window 19c provided on an outer wall of the isothermal bath 19a at a side of the optical convergence adjusting lens unit 22 and forms a circular light path area of diameter D with a center at the light axis 30 on a surface of the reaction cuvette 3. The light having this light path area transmits through the mixed solution S in the reaction cuvette 3 keeping the same shape and transmits through a second transmission window 19d provided on an outside wall of the isothermal bath 19a. The light transmitted through the second transmission window 19d is converged by the optical convergence adjusting lens unit 24 in the optical detection system.

During sample measurement, if any obstacles, such as floating particles in the air or bubbles existing in the isothermal water 19b accidentally flow between the first transmission window 19c of the isothermal bath 19a and one light path area of the reaction cuvette 3, or between the other light path area of the reaction cuvette 3 and the second transmission window 19d of the isothermal bath 19a, the accuracy and precision of the measurement may be influenced by scattering of the transmission light in the light path. However, when the optical converging points of the optical convergence adjusting lens units 22 and 24 are controlled at an infinite distance from the reaction cuvette 3 so as to form parallel light P.L., both a light transmission area of the isothermal bath 19a in front of the reaction cuvette 3 and a light transmission area of the isothermal bath 19a in back of the reaction cuvette 3 becomes a maximum size. This can restrain the occupation ratio of the obstacles against the light transmission area at a relatively lower level. Consequently, the influence of the obstacles can be reduced.

FIG. 8 illustrates the third case where an optical converging point of the optical convergence adjusting lens unit 22 is designated so as to converge at a definite position behind the reaction cuvette 3 on the light axis when the analysis conditions setting screen designates a middle liquid volume Vb that is larger than the minimum liquid volume Vmin and is smaller than the maximum liquid volume Vmax, as a liquid amount of the reactive solution. In this case, the optical converging point of the optical convergence adjusting lens unit 22 is controlled in accordance with the designated middle liquid volume Vb. Thus, in order to converge the optical converging point of the optical convergence adjusting lens unit 22 at a position F a definite distance Lb behind the center of the reaction cuvette 3 a curvature of the inter-surface 228 of the two-layer lens in the optical convergence adjusting lens unit 22 is variably controlled by the control signals from the analysis control unit 40.

The control unit 42 in the analysis control unit 40 obtains the middle height Hb of the mixed solution dispensed in the reaction cuvette by dividing the middle liquid volume Vb with the area A of the reaction cuvette 3, i.e. Vb/A. Further, a variable height of the light path is obtained by subtracting the tolerance height Hmg from the liquid height Hb. Thus, the variable height (Hb−Hmg) of the light path determines an upper limit of the light path area in the reaction cuvette 3 for the optical converging point. By the control signals from the control unit 42, the optical convergence adjusting lens unit 22 converges the light path at a position a distance Lb (Lb>Lmin) on the light axis 30 that is apart from a crossing point between the inter-surface in the optical convergence adjusting lens unit 22 and the light axis 30.

When the liquid volume designated in the analysis conditions setting screen 63 is a middle liquid volume Vf that is larger than the minimum liquid volume Vmin and is smaller than the maximum liquid volume Vmax, as illustrated in FIG. 9, it is possible to be controlled so that the irradiation light is converged at a side of the optical convergence adjusting lens unit 22 in front of the reaction cuvette 3. In this case, the irradiation light is converged at a distance Lf (0<Lf<Lmin) from a crossing point of an inter-surface in the optical convergence adjusting lens unit 22 and the light axis 30. An upper limit of light path area in the reaction cuvette 3 has a variable height Hf that is higher than the minimum height Hmin from the bottom surface in the reaction cuvette 3 and is lower than the maximum height Hmax. Thus, a measurable liquid volume Vf is obtained as the product ((Hf+Hmg)×A), wherein Hmg is the tolerance height and A is an area of the cuvette.

When the turbidimetric measurement is designated as the kind of reaction for the examining substance through the analysis conditions setting screen 63, and also when the liquid volume of the examining solution is larger than the measurable minimum volume Vmin, it is possible to variably control each optical converging point of the respective optical convergence adjusting lens units 22 and 24 so as to maximize or minimize the irradiation numeral aperture (NAi) or the detection numeral aperture (NAd) of the transmitted light to a position other than the center position of the reaction cuvette 3.

In a case where a liquid volume of the reactive solution is a middle liquid volume Vb, light mostly approaching parallel capable of being used to measure the mixed solution is irradiated on the mixed solution in the reaction cuvette 3 by optically converging at an infinite distance from the center of the reaction cuvette 3. By converging the light so that it mostly approaches parallel as it is transmitted through the mixed solution, the influence of the scattered light that creates error factors for the measurement of turbidity change by using the transmission light can be reduced. To reduce the influence of scattered light during the measurement of the mixed solution, the reaction cuvette 3 is irradiated by a light having an energy as large as possible and a transmitted light through the mixed solution is converged so as to have an energy as large as possible.

When the examining substance designated in the analysis conditions setting screen 63 includes a large ratio of the light measuring error factor and requires a high signal to noise (S/N) ratio, S/N ratio data is preliminarily designated as the analysis condition. By variably changing the optical converging points of the adjusting lens units 22 and 24 in accordance with the designated analysis conditions of the liquid volume of the reactive solution, the examining substance is measured with good accuracy and precision.

According to another embodiment of the present invention, the optical converging points of the optical convergence adjusting lens units 22 and 24 to the reaction cuvette 3 contained the mixed solution can variably change in accordance with the liquid volume of the mixed solution for the examining substance against the preliminary designated analysis conditions for the respective examining substance. For instance, the converging points may vary depending on the kind of reaction, i.e., spectrophotometric measurement or turbidimetric measurement, or the liquid properties of the reagent, i.e., viscosity and an easiness of bubbling. In a case where the designated liquid volume of the reactive solution exceeds the minimum liquid volume Vmin, the minimum volume of the mixed solution with the minimum sample volume and the minimum reagent volume can be measured by optically converging at the center position in the reaction cuvette 3.

In a case where the liquid volume of the reactive solution exceeds the maximum liquid volume Vmax, an optical converging point is positioned at an infinite distance from the reaction cuvette 3 and the parallel light transmitted through the mixed solution is detected. By doing so, it becomes possible to restrain the influence of the scattered light that is an error factor for the turbidimetric measurement when using transmission light.

When the liquid amount of the reaction solution is the middle volume Vb, the influence of scattered light that creates an error factor for measuring change of turbidity can be reduced. In this case, the transmitted light is irradiated as nearly parallel light on the reaction cuvette 3 so as to converge at an infinite distance from the center of the reaction cuvette 3 in order to converge the nearly parallel light passed through the mixed solution. Thus, the influence of the scattered light during the measurement of the mixed solution in the reaction cuvette can be reduced by irradiating the maximum amount of energy and by converging the maximum energy of the transmitted light through the mixed solution.

According to the present invention, it becomes possible to measure a very small volume of the mixed solution. Further, even when the designated kind of reaction for the examining ingredient is turbidimetric measurement and an occupation ratio of the light measuring error factors is relatively large and an examining substance requires a high S/N ratio, the accuracy and precision of the measurement can be improved by using the transmission light. Consequently, multiple examining substances can be measured with high accuracy and precision by using a single automatic analysis apparatus.

In the above-mentioned embodiments, while both of the optical convergence adjusting lens unit 22 in the optical irradiation system and the optical convergence adjusting lens unit 24 in the optical detection system are respectively provided in front of and in back of the reaction cuvette 3, either one of the optical convergence adjusting lens units can be eliminated. For instance, when the optical convergence adjusting lens unit 22 is eliminated from the optical irradiation unit 21 in the measurement unit 13, the light transmitted through the mixed solution contained in the reaction cuvette 3 is converged by adjusting the optical convergence adjusting lens unit 24 in the optical detection system based on the analysis conditions designated for the respective examining substances or the analysis conditions inputted through the analysis conditions setting screen 63. On the other hand, when the optical convergence adjusting lens unit 24 in the optical detection unit 23 is eliminated, the optical converging point of the optical convergence adjusting lens unit 22 is variably adjusted so as to irradiate the reaction cuvette 3 based on the analysis conditions designated for the respective examining substances or the analysis conditions inputted through the analysis conditions setting screen 63. In either case, the measurement accuracy and precision of the mixed solution contained in the reaction cuvette 3 can be improved.

As explained above, according to the present invention, it becomes possible to variably adjust the optical converging points of the incident light and transmission light to and from a reaction cuvette in accordance with the volume of the mixed solution contained in the reaction cuvette so as to maximize the area of the irradiation light into the mixed solution. Consequently, the measurement accuracy and precision can be improved and the volume of the reactive fluid can be minimized in accordance with the analysis conditions for the respective examining substance.

Other embodiments will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An automatic analysis apparatus, comprising:
    an optical measurement unit configured to measure substances of examination items in a mixed solution in a reaction cuvette, the mixed solution including an object sample and a reagent, to irradiate light through the reaction cuvette and to detect transmitted light through the reaction cuvette, the optical measurement unit including:
    a light source configured to irradiate light through the reaction cuvette along an optical axis of the optical measurement unit,
    an optical detection unit configured to detect a prescribed wavelength of light transmitted through the reaction cuvette, and
    an optical convergence point adjusting unit provided between the light source and the reaction cuvette, or between the reaction cuvette and the detection unit, and configured to variably adjust a position of an optical convergence point of irradiation light on the optical axis based on an analysis condition for the examination items.

2. The automatic analysis apparatus according to claim 1, further comprising:
    an analysis conditions setting unit configured to set the analysis condition of the examination items;
    the analysis condition includes at least one of a volume of the reaction solution, a wave length of detected light in the optical detection unit, liquid properties of the reagent, and a type of test to be performed on the mixed solution, and
    wherein the optical convergence point adjusting unit is configured to variably change the optical convergence point of the irradiation light onto the reaction cuvette based on the analysis condition.

3. The automatic analysis apparatus according to claim 1, wherein the optical convergence point adjusting unit is configured to variably change an optical convergence point of the irradiation light through the reaction cuvette based on the analysis condition including the type of test to be performed on the mixed solution.

4. The automatic analysis apparatus according to claim 1, wherein the optical convergence point adjusting unit is configured to adjust the optical convergence point of the irradiation light at about a center position of the reaction cuvette, wherein the analysis condition includes a turbidimetric assay as the type of test to be performed on the mixed solution, and the volume of reaction solution is a minimum volume capable of measurement by the automatic analysis apparatus and a measurement tolerance volume.

5. The automatic analysis apparatus according to claim 1, wherein the optical convergence point adjusting unit is configured to set the optical convergence point of the irradiation light at an infinite position so that light transmitted through the reaction cuvette is substantially parallel to the optical axis, and
   wherein the analysis condition includes a turbidimetric assay as the type of test to be performed on the mixed solution and the amount of the reaction solution exceeds the maximum amount for a measurement by the automatic analysis apparatus.

6. The automatic analysis apparatus according to claim 1, wherein the optical convergence point adjusting unit is configured to adjust the optical convergence point of the irradiation light to be in front of the reaction cuvette or behind the reaction cuvette so as to obtain an optimum area of light through the reaction cuvette,
   wherein the analysis condition includes a turbidimetric assay as the type of test to be performed on the mixed solution and the volume of the reaction solution is a middle liquid volume between a maximum volume capable of a measurement and a minimum volume capable of measurement by the automatic analysis apparatus and a measurement tolerance volume.

7. The automatic analysis apparatus according to claim 1, the optical measurement unit further comprising:
   a first optical convergence point adjusting unit provided between the light source and the reaction cuvette configured to variably adjust an optical convergence point of the irradiation light onto the reaction cuvette; and
   a second optical convergence point adjusting unit provided between the reaction cuvette and the optical detection unit configured to variably adjust an optical convergence point of the transmitted light through the reaction cuvette.

8. The automatic analysis apparatus according to claim 7, wherein the second optical convergence point adjusting unit is configured to make the optical convergence point of the transmitted light through the mixed solution and the optical convergence point of the first optical convergence point adjusting unit coincident.

9. An automatic analysis apparatus comprising an optical measurement unit configured to measure ingredients of examination substances in a mixed solution in a reaction cuvette, the mixed solution including an object sample and a reagent, to irradiate light through a reaction cuvette and to detect transmitted light through the reaction cuvette, the optical measurement unit including:
   a light source configured to irradiate light through the reaction cuvette along an optical axis of the optical measurement unit,
   an optical detection unit configured to detect a prescribed wavelength of light transmitted through the reaction cuvette,
   a liquid lens provided between the light source and the optical detection unit, the liquid lens including a plurality of liquid layers having different refractive indexes and a changing unit configured to change an interfacial curvature between the plurality of liquid layers, and
   a control unit configured to control the changing unit in accordance with each analysis condition for respective examination items in order to adjust the optical convergence point of irradiation light through the reaction cuvette.

10. The automatic analysis apparatus according to claim 9, wherein
   the liquid lens further includes,
      a liquid layer,
      an oil layer having a different refractive index from the liquid layer, and
      at least one inter-surface between the liquid layer and the oil layer;
   the changing unit further includes at least one pair of electrodes facing the liquid lens; and
   the control unit is configured to change the interfacial curvature by controlling a voltage supplied to the at least one pair of electrodes.

11. The automatic analysis apparatus according to claim 9, wherein the control unit is configured to control a voltage supplied to the changing unit so that the interfacial curvature is configured to generate irradiation light approximately parallel to the optical axis, and the control unit is configured to perform a turbidimetric assay on the examination items.

12. The automatic analysis apparatus according to claim 9, wherein
   the liquid lens further includes,
      a first oil layer,
      a second oil layer having a different refractive index from the first oil layer, and
      at least one of inter-surface between the first oil layer and the second oil layer;
   the changing unit furthers includes at least one pair of electrodes facing the liquid lens, and
   the control unit is configured to change the interfacial curvature by controlling a voltage supplied to the at least one pair of electrodes.

13. An automatic analysis method for optically measuring ingredients of examination substances in a reaction solution in a reaction cuvette, wherein the reaction solution includes an object sample and a reagent, comprising:
   irradiating light through the reaction cuvette;
   detecting light transmitted through the reaction cuvette,
   variably adjusting an optical convergence point of an optical convergence point adjusting unit provided between a light source and the reaction cuvette, or between the reaction cuvette and a detection optical unit, along an optical axis of an optical measuring unit based on an analysis condition for the examination items.

14. The automatic analysis method according to claim 13, wherein
   the analysis condition includes at least one of a volume of the reaction solution, a wave length of detected light in the optical detection unit, liquid properties of the reagent, and a type of test to be performed on the mixed solution.

15. The automatic analysis method according to claim 13, further comprising:
   maximizing the amount of light transmitted through the reaction cuvette by controlling the optical convergence point and the volume of the reaction solution.

16. The automatic analysis apparatus according to claim 1, wherein the optical convergence point adjusting unit is configured to variably adjust a position of an optical convergence point of the irradiation light on the optical axis so as to maximize an amount of the irradiation light to and from the reaction cuvette based on an analysis conditions for examination items.

17. The automatic analysis apparatus according to claim 2, wherein
- the type of test to be performed on the mixed solution includes a spectrophotometric assay and a turbidimetric assay, and
- the liquid properties of the reagent include viscosity and ease of bubbling the reagent.

18. An automatic analysis apparatus, comprising:
- means for optically measuring substances of examination items in a mixed solution in a reaction cuvette, the mixed solution including an object sample and a reagent, said measuring means including:
  - means for transmitting light through the reaction cuvette along an optical axis of the means for measuring,
  - means for detecting a prescribed wavelength of light transmitted through the reaction cuvette, and
  - means for variably adjusting a position of an optical convergence point of light transmitted through the cuvette on the optical axis based on an analysis condition for the examination items, said means for variably adjusting provided between the means for transmitting light and the reaction cuvette, or between the reaction cuvette and the means for detecting.

19. The automatic analysis apparatus according to claim 18, further comprising:
- means for setting an analysis condition of the examination items;
- the analysis condition including at least one of a volume of the reaction solution, a wave length of detected light by the means for detecting, liquid properties of the reagent, and a type of test to be performed on the mixed solution.

20. The automatic analysis apparatus according to claim 19, wherein
- the type of test to be performed on the mixed solution includes a spectrophotometric assay and a turbidimetric assay.

21. The automatic analysis apparatus according to claim 19, wherein
- the analysis condition is the volume of the reaction solution.

\* \* \* \* \*